US005227565A

United States Patent [19]

Durante et al.

[11] Patent Number: 5,227,565

[45] Date of Patent: Jul. 13, 1993

[54] DIMERIZATION AND/OR DEHYDROGENATION OF ALKANES

[75] Inventors: Vincent A. Durante, West Chester; James E. Lyons, Wallingford, both of Pa.

[73] Assignee: Sun Company, Inc. (R&M), Philadelphia, Pa.

[21] Appl. No.: 906,066

[22] Filed: Jun. 29, 1992

[51] Int. Cl.[5] ........................ C07C 5/327; C07C 5/333

[52] U.S. Cl. .................................... 585/656; 585/661; 585/662; 502/51; 502/38

[58] Field of Search ........................ 585/656, 661, 662; 502/51, 38

[56] References Cited

U.S. PATENT DOCUMENTS 4,172,810 10/1979 Mitchell, III et al. .............. 585/656
5,073,657 12/1991 Warren .............................. 585/657
5,073,664 12/1991 Durante et al. ..................... 585/700

OTHER PUBLICATIONS

Otsuka et al., *Journal of Catalysis* (1990) 121, 122-130.

*Primary Examiner*—Anthony McFarlane
*Assistant Examiner*—Nhat D. Phan
*Attorney, Agent, or Firm*—Q. Todd Dickinson; Donald R. Johnson

[57] ABSTRACT

Barium peroxide oxidizer, together with a transition metal from Group I, III, IV, V, VII or VIII or compound thereof is used as stoichiometric reagent in the oxidative dimerization of hydrocarbons having three or four carbon atoms. Barium peroxide oxidizer, together with a transition metal from Group I, III, IV, V, VI, VII or VIII or compound thereof is used as stoichiometric reagent in the dehydrogenation of hydrocarbons having three or four carbon atoms.

6 Claims, No Drawings

DIMERIZATION AND/OR DEHYDROGENATION OF ALKANES

BACKGROUND OF THE INVENTION

In our U.S. Pat. No. 5,073,664 issued Dec. 17, 1991, a process for the coupling of alkanes at low temperature over a regenerable stoichiometric reagent, barium peroxide, is disclosed and claimed. We have now found that by modifying the peroxide by incorporation of transition metal complexes or salts, reactivity is significantly altered even though levels a low as 1% (wt) of a transition metal are added to the peroxide. New reactions have also been discovered depending on the choice of the added metal.

PRIOR ART

The oxidative coupling of methane to give ethane and ethylene has been widely studied over the past two decades. Among catalysts for this process are the reducible metal oxides such as PbO, MnO, LiO/MgO and many others. They are used with or without promoters. Temperatures required for the process usually exceed 650° C. which is well above the temperature of 450° C. at which the isoparaffin dimers of propane and butane thermally crack.

In *Journal of Catalysis* (1990) pp. 121-122, Otsuka et al indicated that propane coupling could occur at low yield in a stoichiometric anaerobic reaction over sodium peroxide at 375° C. It is, however, difficult to regenerate the reduced sodium product with molecular oxygen.

SUMMARY OF THE INVENTION

According to our invention, hydrocarbons having three or four carbon atoms in the molecule are oxidatively dimerized by contact in a reaction zone with a reagent comprising barium peroxide oxidizer and an added transition metal or compound thereof at a temperature sufficient to oxidatively dimerize the hydrocarbon and reduce the barium peroxide to barium oxide or other by-product, then a branched chain dimer of the hydrocarbon and reduced reagent comprising largely barium oxide and the metal or compound thereof are recovered from the reaction zone, and the reduced barium species is oxidized to regenerate said reagent.

The reaction temperature in the oxidative dimerization is 200° to 450° C., preferably 250° to 400° C., more preferably 300° to 400° C. The reaction can be done in liquid or vapor phase, preferably in the vapor phase, at pressures of 0 to 2000 psig, preferably 400 to 1200 psig. The temperature will vary depending on the processing arrangement and the feedstock, but the minimum temperature necessary is easily determined.

In another embodiment of the invention, hydrocarbons having three or four carbon atoms in the molecule are dehydrogenated by contact in a reaction zone with a reagent comprising barium peroxide oxidizer and an added transition metal or compound thereof at a temperature sufficient to dehydrogenate the hydrocarbon and reduce the barium peroxide to barium oxide or other species, then dehydrogenated hydrocarbon and reduced reagent comprising largely barium oxide and the added metal or compound thereof are recovered from the reaction zone, and the reduced barium species in the reduced reagent is oxidized to regenerate the reagent.

The reaction temperature in this embodiment is 200° to 650° C., preferably 250° to 450° C., more preferably 300° to 400° C. The reaction can be done in liquid or vapor phase at pressures of 0 to 2000 psig, preferably 400 to 1200 psig.

It is possible to simultaneously oxidatively dimerize a portion of the hydrocarbon feed and dehydrogenate another portion of the feed. In such case, hydrocarbons having three or four carbon atoms in the molecule are contacted in a reaction zone with a reagent comprising barium peroxide oxidizer and a transition metal or compound thereof at a temperature sufficient to oxidatively dimerize part of the feed and dehydrogenate another part of the feed and reduce the barium peroxide to barium oxide, then branched chain dimer, dehydrogenated hydrocarbon, and reduced reagent comprising largely barium oxide and the added metal or compound thereof are recovered from the reaction zone, and the reduced barium reagent is oxidized to regenerate the reagent. Temperature and pressure for this embodiment are generally the same as for the oxidative dimerization embodiment above.

DETAILED DESCRIPTION OF THE INVENTION

Barium peroxide is an article of commerce and readily available. It can be made by the direct combustion of barium or barium oxide in air or oxygen at 500° to 600° C. Because of this, the lower oxides of barium formed from the barium peroxide, $BaO_2$, in the oxidative dimerization and/or dehydrogenation of this invention are readily regenerable to barium peroxide.

Barium peroxide may be doped with metal by several techniques. Presynthesized or purchased barium peroxide may be doped with metal by impregnation with aqueous solutions of metal salts or complexes. For example, iron (II) tetrafluoroborate (aqueous), chromic nitrate, manganese (II) nitrate, or polynuclear metal complexes such as heteropoly acids (typically Keggin or Dawson structures), or other polynuclear metal species, particularly those containing iron or ruthenium and at least one labile ligand may be used. Alternatively, barium plus metal can be coprecipitated followed by treatment with concentrated hydrogen peroxide or with oxygen at high temperature to form the peroxides. A variable amount of barium carbonate, barium bicarbonate, or barium oxide may also be present.

EXAMPLES

Experiments were performed in which a pulse of an alkane such as isobutane or propane was passed over the doped peroxides at high pressure and at moderate temperatures. On-line analytical systems indicated the products to be dehydrogenation, coupling, cracking or combustion products, as shown in Table 1 infra.

TABLE 1

SUMMARY OF HIGH PRESSURE, ANAEROBIC PULSE REACTOR EXPERIMENTS:[a]
STOICHIMETRIC REACTIONS OF ALKANES WITH PROMOTED BARIUM PEROXIDES[b]

| | Carbon Selectivity | | | Coupling | |
|---|---|---|---|---|---|
| Conversion per | C—C | frag[f] or | com- bust | Isomer Ratio | Observa- |

TABLE 1-continued

SUMMARY OF HIGH PRESSURE, ANAEROBIC PULSE REACTOR EXPERIMENTS:[a] STOICHIMETRIC REACTIONS OF ALKANES WITH PROMOTED BARIUM PEROXIDES[b]

| Run | H-Acceptor | Feed | T[n] (°C.) | P[c,m] psig | Pulse (mol %) | coupling[d] | dehyd[e] (atomic % of conv. C) | cracking | CO[x] | (i-i-i:t-t-t:other)[g] | tions/ Comments |
|---|---|---|---|---|---|---|---|---|---|---|---|
| 1 | CdO[h] | $C_3H_8$ | 614 | 1512 | 32.6 | trace | 17.6 | 42.9 | 24.8 | | bz, tol obs'd |
| 2 | | | 375 | 1513 | 0.8 | 0 | 18.0 | 28.5 | 6.3 | | no aromatics |
| 3 | $BaO_2$ | $CH_4$ | <501 | 814 | 0 | 0 | 0 | 0 | 0 | | $O_2$ obs'd |
| 4 | | $C_3H_8$ | 398 | 800 | ca6 | 33 | some | | 0 | 1:1.36:0.08[i] | $H_2O$, $C_4$, $C_3$ |
| 5 | | $iC_4H_{10}$ | 400 | 810 | low | low | ? | ? | ? | | |
| 6 | 1% Fe/BaO2 | $CH_4$ | ≦501 | 815 | | low | | | | | $C_2$ obs'd at T > 475° |
| 7 | | $iC_4H_{10}$ | 313 | 815 | 4.9 | 62.0 | 31.5 | trace | 0 | | trace $O_2$ $C_3$'s, tr$CH_4$ |
| 8 | | j | 343 | | 20.2 | 72.9 | 22.4 | <4[k] | 0 | 1:1.82:[l] 1.14:0.19 | (1st pulse) |
| | | | 346 | | 12.0 | 73.7 | 20.8 | k | 0 | | (2nd pulse) |
| | | | 346 | | 9.3 | 70.8 | 24 | k | 0 | | (3rd pulse) |
| 9 | | | 368 | | 17.7 | 69.9 | 20.8 | k | 0 | | |
| 10 | | | 399 | | 16.2 | 51.2 | 34.8 | k | 0 | | |
| 11 | 1% Cr/Ba02 | $iC_4H_{10}$ | 345 | 818 | 4.6 | 0 | ca95 | | | | |
| 12 | 1% Ce/$BaO_2$ | $CH_4$ | <500 | 815 | | low | | | | | $C_2$ obs'd at T > 430° |
| 13 | | $iC_4H_{10}$ | 349 | 813 | 2.9 | 64.8 | 35.2 | | | | |
| 14 | | | 398 | | 5.8 | 60.4 | 32.1 | 0 | 0 | | |
| 15 | 1% Ag/$BaO_2$ | $iC_4H_{10}$ | 340 | 815 | 1.1 | 40.4 | 59.6 | | 0 | | |

[a]Packed bed reactor operated isothermally: 400 microliter pulses of prevaporized feedstock injected via automatic valve into flowing He carrier gas (400 ml/min. NTP): granulated oxides (18/35 mesh) mixed 1:1 (v:v) with silica gel diluent: pulse profile and continuous component identification with time detected with on-line quadrupole mass spectrometer operated at low voltage ionization currents (12 V typically) coupled to reactor system through an open-split interface (5 ml/min He): detailed product analysis and quantification performed by capturing slices of the effluent at various points along the effluent peak profile by way of a computer timed sampling valve which feeds three independent multidimensional GC analysis systems including a Pd thimble for $H_2$ analysis, back-flushed packed bed columns/TCD detector for analysis of fixed gases, and a capillary GC/mass spectrometer detector for hydrocarbon products. Identification of products was accomplished by spiking to establish retention times of known compounds and by computer-based comparision to library mass spectral cracking patterns in a commercial data base. Typical pulse dosage was 62 gram-atoms oxide per mole of hydrocarbon pulse. Samples were pretreated at 375° C. to remove superoxide impurities and each pulse was followed by a TPD experiment to look for strongly held absorbates up to 500° C. typically.

[b]Promoted barium peroxides were prepared by aqueous impregnation of commercial granulated $BaO_2$ with ferrous tetrafluoroborate (or $BF_4^-$ salts of other metal ions) to appropriate levels followed by vacuum drying at 90° C. for 12 hours.

[c]0.101 MPa = 14.7 psi = 1 bar.

[d]$C_8$ isomers for I-$C_4H_{10}$ feed runs; $C_6$ products for $C_3H_8$ feed runs; $C_2$ products for $CH_4$ runs; ethylene glycol for $CH_3OH$ feed runs.

[e]Isobutene or propene for isobutane or propane feedstocks respectively.

[f]For isobutane feed, fragmentation products include propene, propane, ethylene, ethane, methane; for propane feed, fragmentation products include ethylene, ethane, methane.

[g]coupled product isomers include:

| isobutane feed | propane feed |
|---|---|
| internal-internal: 2,2,3,3,-tetramethylbutane, (3°-3°) | 2,3-dimethylbutane, (2°-2°) |
| internal-terminal: 2,2,4-trimethylpentane, (3°-1°) | 2-methylpentane, (2°-1°) |
| terminal-terminal: 2,5-dimethylhexane, (1°-1°) | n-hexane, (1°-1°) |

[h]CdO was not diluted with silica gel.

[i,l]Expected ratios of coupling products can be calculated based on statistical availability of C—H, corrected for relative abstraction rates for differend C—H types, and corrected for differences in recombination rates influenced by steric constraints in radical intermediates which must come together:

| | COUPLING PRODUCT | STATISTICAL AVAILABILITY OF C—H | AVAILABILITY[p] & REL. ABSTR. RATE | LITERATURE[q] GAS PHASE ABSTR. & RECOMB. | FOUND THIS STUDY |
|---|---|---|---|---|---|
| i-$C_4H_{10}$ | | | | | |
| | 3°-3° (i-i) | 1 | 1 | 1 | 1 |
| | 3°-1° (i-i) | 9 | 0.12 | 0.38 | 1.82 |
| | 1°-1° (i-i) | 81 | 0.015 | 0.046 | 1.14 |
| | other $C_8$ | — | — | — | 0.19 |
| $C_3H_8$ | | | | | |
| | 2°-2° (i-i) | 1 | 1 | — | 1 |
| | 2°-1° (i-i) | 3 | 0.04 | — | 1.36 |
| | 1°-1° (i-i) | 9 | 0.0014 | — | 0.08 |

[j]Repetitive pulses over same sample.

[k]Major fragmentation product was propene; only a trace of $CH_4$ observed.

[m]±3 psig typical during run.

[n]±2° C. typical during run.

[o]$O_2$ desorbed 430–513° C.

[p]E. W. R. Steacle, Atom and Free Radical Reactions, vol II. Reinhold Publ., NY, 1954, pp. 500.

[q]B. deB. Darwent and C. A. Winkler, J. Phys. Chem. (1945) 49. 150.

Doping of barium peroxide with 1% iron resulted in significant enhancement of dehydrogenation selectivity and overall yield compared to undoped barium peroxide when pulsed with isobutane; no carbon oxides and few cracking products were observed at 300°–400 degrees C. and about 800 psig. In contrast, addition of 1% Cr to $BaO_2$ resulted in significant enhancement of dehydrogenation selectivity but in no coupling. Ce and Ag doped samples are also shown in Table 1. These results are surprising and indicate that a process can be tailored to either dehydrogenation or coupling depending on choice of dopant. $C_6$ and $C_8$ branched isomers produced by this invention are desirable nonaromatic high octane components in motor fuels.

Referring further to Table 1, Runs 1 and 2 show that use of a reducible oxide such as cadmium oxide resulted in only a trace of coupling of propane feed, but significant amounts of dehydrogenation and cracking products.

Runs 3, 4 and 5 show that with undoped barium peroxide, 33% selectivity for coupling of propane is obtained at 398° C. and 800 psig, while with methane and isobutane at <501° C. and 400° C. respectively, there was little or no activity for the undoped barium peroxide.

Runs 6 to 10 inclusive show that barium peroxide doped with 1% iron gave good selectivity for coupling of isobutane, in contrast to the results for the undoped barium peroxide, as well as substantial activity for dehydrogenation of isobutane. It is expected that the results for the iron-doped barium peroxide would also be much better than for the undoped barium peroxide, with propane a feed.

Run 11 shows that barium peroxide doped with 1% chromium, has high activity for dehydrogenation of isobutane, but substantially no activity for coupling of isobutane under the conditions employed.

Runs 12, 13 and 14 show that barium peroxide doped with 1% cerium has good activity for the coupling of isobutane and substantial activity for the dehydrogenation of isobutane as well. It is expected that similar results would be obtained with other $C_3$ or $C_4$ feeds.

Run 15 shows that barium peroxide doped with 1% silver has good activity both for the coupling of isobutane and for the dehydrogenation of isobutane. Similar results are expected for other $C_3$ to $C_4$ feeds.

As described in the 664 patent supra for undoped barium peroxide, the used metal-doped peroxide reagents can be regenerated with air or oxygen under appropriate conditions. Useful temperatures are 200°–600° C. (depending on the reactivity of the system and stability of the coupled or dehydrogenated hydrocarbons), preferably 300°–400° C. Useful pressures are 0.1 to 1000 atmospheres, preferably 30–65 atmospheres.

The process according to the invention can be carried out either cyclically or continuously, as disclosed in the 664 patent supra, the disclosure of which is hereby incorporated by reference.

If oxygen is introduced into the reaction, oxidative dehydrogenation is promoted, but the effectiveness of the process for coupling is reduced.

The results of the examples above indicate that although most reducible metal oxides and solid "catalysts" for methane coupling are not effective at generating light alkane radical coupling or dehydrogenation products at <500° C., barium peroxide and its derivatives promoted with certain +2/+3 transition metal salts are efficient reagents for such conversions at temperatures of 300°–400° C., which are below the thermal cracking range of isodimers. Low level doping of barium peroxide with $Fe^{2+}$ (1 wt. %) resulted in enhanced alkane coupling selectivity; whereas doping with $Cr^{3+}$ resulted in enhanced dehydrogenation selectivity in pulse experiments.

Examination of isomer distributions among isobutane or propane coupling products from pulse experiments indicated the predominance of internal-terminal coupled products (2,2,4-trimethylpentane or 2-methylpentane respectively). This finding is in contrast to literature reports of the competitive gas phase carbon fragment formation and radical coupling rates which result in the internal-internal products (2,2,3,3-tetramethylbutane or 2,3-dimethylbutane respectively) to be predominant products in the absence of a surface interaction. The observed isomer distributions from iron doped peroxide were also in contrast to our results measured in fluid benzene solution in which the 2°–2° coupling product is formed nearly exclusively from propane reacting in the presence of t-butoxy radical. We conclude that there was some involvement of the surface in the vapor phase coupling process over iron doped peroxides which lead to a steric constraint for 3°–3° coupling. Surface (barium oxide) ester intermediates are hypothetical precursors to such coupling products.

Although no carbon oxides are observed in stoichiometric pulse experiments, spectroscopic examination of the surface of the iron-doped peroxide reagents indicated an increase in carbonate carbon to barium ratio from which it appears that at least some carbon dioxide is initially formed along with coupling and dehydrogenation products.

XPS measurements of a 10% $Fe^{2+}/BaO_2$ surface indicated that both +2 and +3 (possibly $FeO_2$) oxidation states of iron existed simultaneously on the surface.

Transition metal compounds which may be used in the reagents for use according to the invention include compounds of copper, silver, titanium, zirconium, vanadium, chromium, molybdenum, tungsten, iron, cobalt, nickel, ruthenium, rhodium, palladium, osmium, iridium, platinum, lanthanum, cerium, praseodymium, gadolinium, dysprosium. For oxidative dimerization, the Group VI metal, chromium, is not suitable, as shown in Run 11 in Table 1, but chromium is highly active for dehydrogenation, as shown in that run. For oxidative dimerization, transition metals from Groups I, III, IV, V, VII and VIII, and preferably from Groups I and VIII, are used, while for dehydrogenation, transition metals from Groups I, III, IV, V, VI, VII and VIII, and preferably from Groups I, VI and VIII, are used. Group IIB metals suitable for use with barium peroxide in dehydrogenation of hydrocarbons are zinc, cadmium and mercury.

The invention claimed is:

1. Process for dehydrogenating branched-chain paraffins which comprises contacting a $C_3$ to $C_4$ hydrocarbon with a reagent comprising barium peroxide oxidizer and a transition metal from Groups I, III, IV, V, VI, VII or VIII of the Periodic Table or compound thereof, in a reaction zone at a temperature sufficient to dehydrogenate said hydrocarbon, recovering a dehydrogenated hydrocarbon and barium oxide from the reaction zone, and regenerating said oxidizer by oxidizing said barium oxide to barium peroxide.

2. Process according to claim 1 wherein said metal is iron.

3. Process according to claim 1 wherein said metal is chromium.

4. Process according to claim 1 wherein said metal is cerium.

5. Process according to claim 1 wherein said metal is silver.

6. Process according to claim 1 wherein said regenerating is by heating the barium oxide in the presence of oxygen at a temperature above 400° C.

* * * * *